US006975943B2

(12) United States Patent
Gibbs et al.

(10) Patent No.: US 6,975,943 B2
(45) Date of Patent: Dec. 13, 2005

(54) CLONE-ARRAY POOLED SHOTGUN STRATEGY FOR NUCLEIC ACID SEQUENCING

(75) Inventors: Richard Gibbs, Houston, TX (US); Allan Bradley, Cambridge (GB); Wei-Wen Cai, Houston, TX (US)

(73) Assignee: Seqwright, Inc., Houston, TX (US)

( * ) Notice: Subject to any disclaimer, the term of this patent is extended or adjusted under 35 U.S.C. 154(b) by 431 days.

(21) Appl. No.: 09/969,111

(22) Filed: Sep. 24, 2001

(65) Prior Publication Data

US 2003/0092007 A1 May 15, 2003

(51) Int. Cl.[7] ......................... G06F 19/00; G01N 33/48; C12Q 1/68

(52) U.S. Cl. ................................ 702/20; 702/19; 435/6

(58) Field of Search .......................... 702/19, 20; 435/6

(56) References Cited

U.S. PATENT DOCUMENTS

| | | | |
|---|---|---|---|
| 6,187,544 | B1 | 2/2001 | Bergsma et al. |
| 2001/0046669 | A1 | 11/2001 | McCobmie et al. |
| 2003/0157546 | A1 | 8/2003 | McCombie et al. |
| 2003/0180750 | A1 | 9/2003 | McCombie et al. |

OTHER PUBLICATIONS

Weber et al. (Genome Research (1997) vol. 7, pp. 401–409).*

Klysik et al. (Genomics (1999) vol. 62, pp. 123–128).*

Shizuya et al. (PNAS (1992) vol. 86, pp. 8794–8797).*

Lee, et al., "Genomic analysis", *Current Opinion in Biotechnology*, vol. 11, pp. 171–175, 2000.

Ishiguro, et al., "fluorescence detection of specific sequence of nucleic acids by oxazole yellow–linked oligonucleotides. Homogeneous quantitative monitoring of in vitro transcription", *Nucleic Acids Research*, vol. 24, No. 24, pp. 4992–4997, Dec. 15, 1996.

Yu, et al., "Large–Scale Concatenation cDNA Sequencing", *Genome Research*, vol. 7., No. 4, pp. 353–358, Apr. 1997.

Cai, et al., "A Clone–Array Pooled Shotgun Strategy for Sequencing Large Genomes", *Genome Research*, vol. 11, pp. 1619–1623, 2001.

Batzolglou, et al., "Sequencing a Genome by Walking with Clone–End Sequences: A Mathematical Analysis", *Genome Research*, vol. 9, pp. 1163–1174, 1999.

Radelof, et al., "Preselection of shotgun clones by oligonucleotide fingerprintin: an efficient and high throughput strategy to reduce redundancy in large–scale sequencing projects", *Nucleic Acids Research*, vol. 26, No. 23, pp. 5358–5364, 1998.

Adams, M.D., Celniker, S.E., Holt, R.A., Evans, C.A., Gocayne, J.D., et al. 2000. The genome sequence of *Drosophila melanogaster. Science* 287:2185–95.

Battey, J., Jordan, E., Cox, D., Dove, W. 1999. An action plan for mouse genomics. *Nature Genet*. 21:73–5.

Bonfield, J.K., Smith, K.F. and Staden, R. 1995. A new DNA sequence assembly program. *Nucleic Acids Res*. 24, 4992–4999.

Cai, W.W., Chow, C.W., Damani, S., Simon, G., and Bradley, A. 2001. A SSLP anchored BAC framework map of the mouse genome. *Nature Genetics* (accepted).

Myers, E.W., Sutton, G.G., Delcher, A.L., Dew, I.M., Fasulo, D.P., et al. 2000. A whole–genome assembly of Drosophila. *Science* 287: 2196–204.

Venter, J.C., et al. (2001). The sequence of the human genome. *Science* 291:1304–51.

Weber, J.L., Myers, E.W. 1997. Human whole–genome shotgun sequencing. *Genome Res*. 7: 401–409.

Yu, W., Andersson, B, Worley, K.C., et al. 1997. Large–scale concatenation cDNA sequencing. *Genome Res*. 7:353–358.

* cited by examiner

*Primary Examiner*—Marjorie Moran
*Assistant Examiner*—Lori A. Clow
(74) *Attorney, Agent, or Firm*—Morrison & Foerster LLP

(57) ABSTRACT

A simplified strategy for sequencing large genomes has been developed. Clone-Array Pooled Shotgun Sequencing (CAPSS) is based upon pooling rows and columns of arrayed genomic clones, for shotgun library construction. Random sequences are accumulated and the data are assembled by sequential comparison of rows and columns, to resolve the sequence of clones at points of intersection. Compared to either a clone-by-clone approach or whole genome shotgun sequencing, CAPSS requires relatively few library constructions and only minimal computational power for a complete genome assembly. The strategy is suitable for sequencing large genomes for which there are no sequence-ready maps, but for which relatively high resolution STS maps and highly redundant BAC libraries are available. It is immediately applicable to the sequencing of mouse, rat, zebra fish and other important genomes, and can be managed in a cooperative fashion to take advantage of the distributed international DNA sequencing capacity.

58 Claims, 2 Drawing Sheets

CLONE-ARRAY POOLED SHOTGUN STRATEGY FOR NUCLEIC ACID SEQUENCING

STATEMENT OF GOVERNMENT RIGHTS

The invention was made with government support under U.S. Government Grant No. R21 CA83211 awarded by the National Institutes of Health. The government has certain rights in the invention.

TECHNICAL FIELD

This invention relates generally to methods for large-scale nucleic acid sequencing, and more particularly to methods for sequencing the genome of an organism.

BACKGROUND

A primary goal of any genomic sequencing project is to determine the entire DNA sequence for a target organism. A related goal is to construct ordered clone maps of DNA sequences at 100 kilobase (kb) resolution for these organisms (D. R. Cox, et al., *Science,* 265:2031, 1994). Integrated maps that localize clones together with polymorphic genetic markers are particularly useful for positionally cloning human disease genes (F. Collins, *Nature Genet.,* 1:3, 1992). Strategies for large-scale genomic DNA sequencing currently require physical mapping, followed by detailed mapping, and finally sequencing. The level of mapping detail determines the amount of effort, or sequence redundancy, required to finish a project. Efficient strategies for performing the requisite experimentation are critical for sequencing and mapping chromosomes or entire genomes. Current strategies attempt to find a balance between mapping and sequencing efforts.

The starting point for an effective sequencing method is a complete ordered clone map of a genome. Putting together the cloned genome requires ordering and linking together all of the clones comprising the genomic DNA library. Mapping strategies can be "top-down" or "bottom-up". The "top-down" strategy depends on the separation on pulsed field gels of large DNA fragments generated using rare restriction endonucleases for physical linkage of DNA markers and construction of a long-range map. The "bottom-up" strategy depends on identifying overlapping sequences in a large number of randomly selected clones by unique restriction enzyme "fingerprinting" and their assembly into overlapping sets of clones. The linking of these clones is not done physically, but in computers and requires the analysis of thousands of individual clones to generate complete maps. This process is labor intensive and expensive because the difficulties increase rapidly with larger genomes, requiring continual advances in mapping approaches, instrumentation and computational expertise (See, e.g., Venter et al., *Science* 280:1540, 1998). Regardless of the linking strategy, the common prior art approach relied on using as large of a fragment as possible in order to minimize the numbers of "puzzle pieces" that had to be linked to obtain the genomic map.

Current strategies for ordering clones build contiguous sequences (contigs) by reassembling contiguous stretches of DNA (See, e.g., Watson, J. D. et al (1992) Recombinant DNA, (W.H. Freeman and Company, New York), pp. 583–618) using short-range comparison data. The number of experiments needed for any short-range clone mapping approach increases with the number of clones in the library. A useful goal is to significantly reduce cost and increase throughput by achieving a number of required experiments largely independent of library size. For example, contigs of small genomic regions have been constructed by oligonucleotide fingerprinting of gridded cosmid filters (A. G. Craig et al., *Nucleic Acids Res.,* 18:2653, 1990). However, complex hybridization probes generate data containing considerable noise, thus precluding high-resolution mapping of clones using this technique.

Currently, two competing strategies are being used to sequence the large genomes. The clone-by-clone (CBC) strategy has produced highly accurate sequences of *E. coli* (Blattner et al., *Science* 277:1453, 1997), yeast (Goffeau et al., *Science* 274:546, 1996), human chromosomes 22 (Dunham et al., *Nature* 402:489, 2000) and 21(Hattori et al., *Nature* 405:311, 2000), and draft sequence covering about 90% of the human genome. These successes have largely benefited from the construction of sequence-ready maps. For future projects such as the mouse genome, for which map resources are relatively scarce, the advantage of this strategy will be less obvious. The whole genome shotgun (WGS) strategy involves sequencing all of the naturally occurring DNA sequences (i.e. genomic DNA) constituting the genome of an organism without prior mapping of large clones. WGS sequencing essentially involves randomly breaking DNA into segments of various sizes and cloning these fragments into vectors. The clones are sequenced from both ends improving the efficiency of sequence overlapping assembly.

WGS obviates the need for a sequence-ready map, but relies heavily on immense computational power for assembling random shotgun reads into long continuous sequence contigs, which are finally anchored to chromosomes using other mapped sequence information. Recent success in applying this strategy to sequence the 120 Mb euchromatic portion of Drosophila genome provides proof of principle for WGS (Adams et al., *Science* 287:2185, 2000). This impressive achievement does not, however, guarantee that the strategy will work on the human or mouse genome. Each is more than 20 times larger than Drosophila and the computational requirements to perform the necessary pairwise comparisons increase approximately as a square of the size of the genome. Indeed, the reported experience with the Drosophila WGS (Myers et al., *Science* 287:2196, 2000) indicates the achievable computational power will not be sufficient to assemble the human genome sequence purely from shotgun random reads and that inevitably binned sequence reads from the individual bacterial artificial chromosomes (BACs) in the public data base will have to be used to anchor the whole genome shotgun random reads in order to resolve ambiguities and lower the computational load.

As can be seen from the foregoing discussion, determining the complete sequence of complex mammalian or plant genomes to a high standard of accuracy remains a considerable problem. Thus, a need exists in the art for a sequencing method that can lead to the rapid identification of genes and regulatory sequences in complex eukaryotic genomes. In particular, there is a need to reduce the amount of computing power needed to sequence complex genomes. The present invention provides methods and systems for determining the sequence of the genome of an organism or species through the use of a novel, unobvious, and highly effective clone array pooled shotgun strategy. Such sequence information can be used for finding genes of known utility, determining structure/function properties of genes and their products, elucidating metabolic networks, understanding the growth and development of humans and other organisms, and making comparisons of genetic information between species. From these studies, diagnostic tests and pharmacological agents can be developed of great utility for preventing and treating human and other disease.

SUMMARY

The present invention provides unique methods and systems for sequencing extensive nucleic acid sequences such as, for example, those sequences found in the genome of an organism. The methods are based upon pooling rows and columns of arrayed clones for shotgun library construction. Data are assembled by sequential comparison of rows and columns thereby resolving the sequence of clones at points of intersection. Thus, in one embodiment, the invention provides a method for determining the sequence of a nucleic acid present in a clone by providing a plurality of clones in an array including predetermined axis, whereby the position of each clone in the array may be identified; pooling multiple clones of a first axis and preparing a first library from the pooled clones; performing random reads on the pooled clones, thereby generating sequence coverage of the pooled clones; pooling multiple clones of a second axis and preparing a second library from the pooled clones, wherein the second axis intersects the first axis at a nexus, and wherein the nexus includes at least one clone that is common to the first and second axis; performing random reads on the pooled clones of the second axis thereby generating sequence coverage of the pooled clones; cross-assembling the random reads of the first axis with the random reads of the second axis, thereby generating a sequence contig associated with the nucleic acid present in the nexus clone; and combining contigs to construct a map of the nexus clone; and determining the sequence of the nucleic acid present in the clone.

Nucleic acid present in the plurality of clones can collectively represent the genomic complement of an organism. Each clone of a plurality of clones present in the array can be compartmentalized and the location of each clone in the array is identifiable by unique coordinates. For example, a two-dimensional array can identify clones in an x axis and a y axis coordinate. Alternatively, an array of the invention can be a three-dimensional array that includes coordinates identifiable in an x axis, a y axis and a z axis. Intersecting planes of two or more axis represents a nexus. Each random read generates about 3 to 12 fold coverage of the nexus clone.

The clones of the present invention typically represent a library having at least two-fold coverage of a genome and comprised of bacterial, yeast or phage cloning vectors. More particularly, the vector is selected from a BAC, YAC, megaYAC or PAC vector. The DNA insert present in a clone can range from 50 bp to 5 Mbp. The average DNA insert size of about 125 kbp to 500 kbp. A genome includes a mammalian genome such as, for example, a mouse genome. Each clone can be contained in a cell such as a bacterial cell, a yeast cell or a mammalian cell.

In another embodiment, the invention provides a method for physical mapping of a genome including preparing a genomic library comprising a plurality of clones by inserting DNA fragments from a genome into vectors; arranging the clones in an array in predetermined axis, whereby the position of each clone in the array may be identified; pooling the clones of a first axis and preparing a first library from the pooled clones; performing random reads on the pooled clones of the first axis, thereby generating sequence coverage of the pooled clones; pooling the clones of a second axis and preparing a second library from the pooled clones, wherein the second axis intersects the first axis at a nexus, and wherein the nexus comprises at least one clone that is common to the first and second axis; performing random reads on the pooled clones of the second axis, thereby generating sequence coverage of the pooled clones; cross-assembling the random reads of the first axis with the random reads of the second axis and identifying contiguous regions among the cross-assembled random reads thereby generating a contig map.

In another embodiment, the invention provides a system for sequencing a genome including: a means or mechanism for arranging a plurality of clones in a array, wherein the array includes predetermined axis and wherein each clone is identifiable in the array; a means or mechanism for pooling clones of a first axis and preparing a first library from the pooled clones; a means or mechanism for performing random reads on the pooled clones of the first axis, thereby generating sequence coverage of the pooled clones; a means or mechanism for pooling the clones of a second axis and preparing a second library from the pooled clones, wherein the second axis intersects the first axis at a nexus, and wherein the nexus includes at least one clone that is common to the first and second axis; a means of mechanism for performing random reads on the pooled clones of the second axis, thereby generating sequence coverage of the pooled clones; a means or mechanism for cross-assembling the random reads of the first axis with the random reads of the second axis, thereby generating a sequence contig associated with the nucleic acid present in the nexus clone; a means or mechanism for combining multiple sequence contigs derived from a plurality of nexuses to construct a map of the clones relative to the genome; and a means or mechanism for determining the sequence of the genome by means of the map.

In yet another embodiment, the invention provides a computer-assisted method for determining the sequence of a genome using a programmed computer including a processor, an input device, and an output device, the method including: inputting into the programmed computer, through the input device, data including the location of each clone of a plurality of clones in an array comprising predetermined axis, wherein the location of each clone is identified by unique coordinates that describe the position of each clone in the array, and wherein the plurality of clones collectively represent the genome of an organism; inputting, into the programmed computer, the coordinates of the clones of a first axis that are pooled; inputting, into the programmed computer, the coordinates of the clones of a second axis that are pooled; determining, using the processor, the intersection of the first axis of pooled clones with the second axis of pooled clones thereby identifying a nexus coordinate including at least one clone that is common to the first and second axis; inputting, into the programmed computer, sequence information generated by random reads of the pooled clones of the first axis; inputting, into the programmed computer, sequence information generated by random reads of the pooled clones of the first axis; cross-assembling, using the processor, the random reads of the first axis with the random reads of the second axis, thereby generating a sequence contig associated with the nucleic acid present in the nexus clone; combining, using the processor, multiple sequence contigs derived from a plurality of nexuses to construct a map of the clones relative to the genome; and determining, using the processor, the sequence of the genome and outputting, to the output device, the results of the determination.

In another embodiment, the invention provides a multi-user method for sequencing a genome, including: providing a first user with a plurality of clones from a first axis of an array representing a portion of the genomic DNA of an organism; providing a second user with a plurality of clones from a second axis of an array representing a portion of the genomic DNA of an organism, wherein the second axis intersects the first axis at a nexus, and wherein the nexus comprises at least one clone that is common to the first and second axis; providing the first user with a mechanism for communicating a sequence generated from the array; providing the second user with a mechanism for communicating a sequence generated from the first axis; allowing the first and second user to transmit the sequence to a shared server; obtaining the transmitted sequences provided by the users; inputting into a programmed computer, through an input device, data including the sequences; cross-assembling, using the processor, the sequences and determining a sequence contig associated with the sequence; and outputting, to the output device, the results of the at least one determination.

In yet another embodiment, the invention provides a method for indexing a nucleic acid sequence of an organism including: providing a first sequence from a first organism according to the a method of the invention; indexing the sequence of the first organism;

comparing the indexed sequence of the first organism with a non-indexed sequence obtained from a second organism; and identifying a sequence in the non-indexed sequence which is common to the indexed sequence, thereby indexing the non-indexed sequence of the second organism.

The invention further provides a computer system including a database incorporating records of the location of each clone of a plurality of clones in an array having predetermined axis; a database including random reads of the clones inputted by one or more users of the database; a processor for cross-assembling the random reads of the clones; a processor for determining contiguous regions among the cross-assembled random reads and for generating a contig map based upon the identified contiguous regions; and a means for outputting to an output device the results of the contig map.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
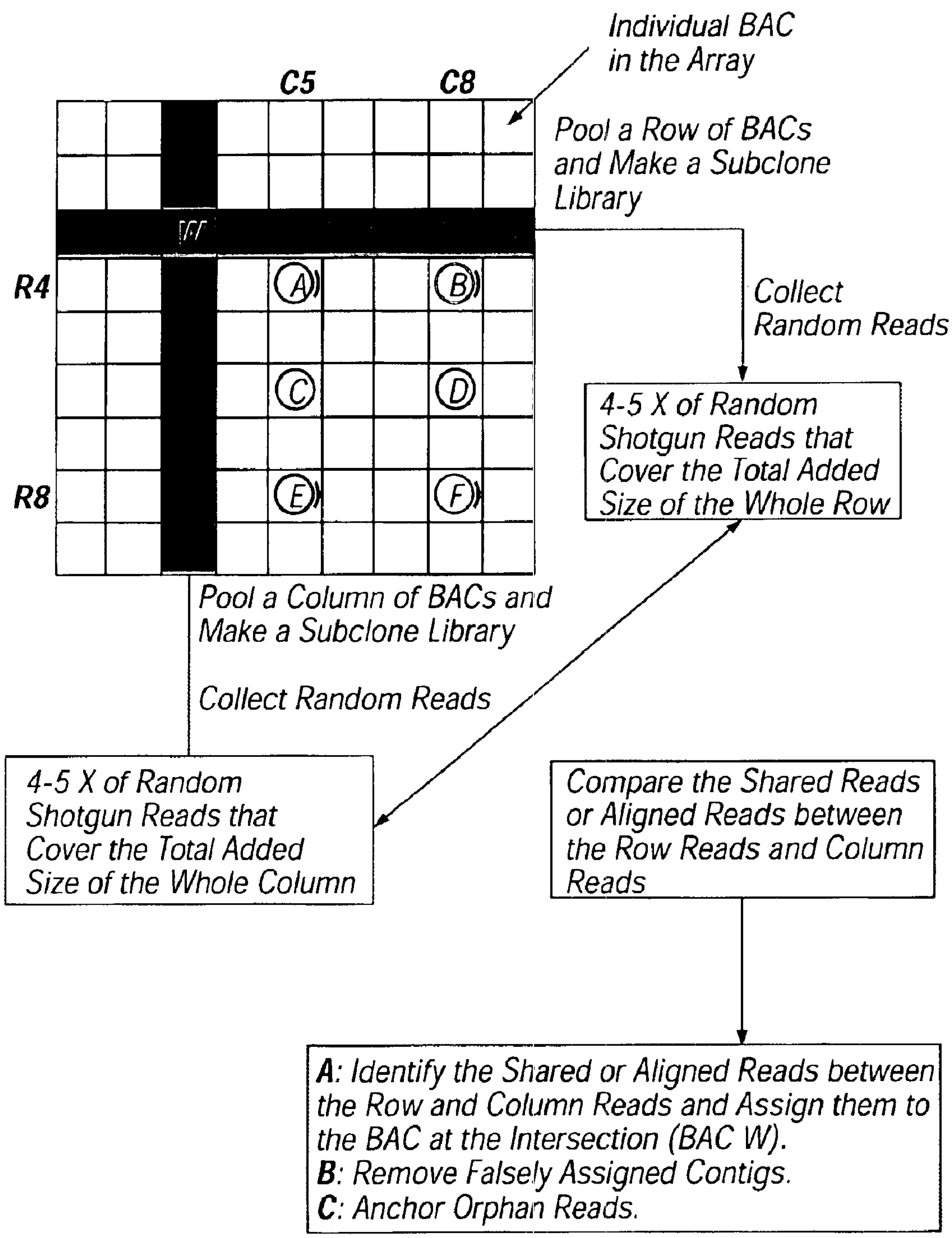
FIG. 1 depicts the general clone array pooled shotgun sequencing (CAPSS) strategy. Genomic clones are organized in an array, and pools of DNA from each row and column are converted to a subclone library for sequencing. The sequence assembly of each clone is generated by cross-assembly of each row and column, shown as clone W in this schema.

The present invention provides rapid and economical methods and systems suitable for the generation, collection, organization, indexing, storage, and analysis of nucleic acid sequences. The invention facilitates the acquisition of knowledge concerning the pathways, functions, and interactions of these sequences (functional genomics) and their encoded proteins (proteomics).

Complete analysis of an organism's genome requires extensive isolation, purification and analysis of fragments of DNA to create genomic libraries. Typically fragments as large as possible are used to minimize the number necessary to comprise the genome. The cloning systems used to generate these genomic libraries include the use of bacteriophage, cosmid, BAC, YAC and P1 vectors. The analysis of complex genomes involves the application of both "top-down" and "bottom-up" mapping strategies. The "top-down" strategy depends on the separation on pulsed field gels of large DNA fragments generated using rare restriction endonucleases for physical linkage of DNA markers and the construction of long-range maps. The "bottom-up" strategy depends on identifying overlapping sequences in a large number of randomly selected clones by unique restriction enzyme fingerprinting and their assembly into overlapping sets of clones. "Top down" mapping is inherently more rapid and less labor intensive, but does not generate sets of DNA clones for further structural or biological analysis. "Bottom-up" mapping generates the required sets of overlapping clones but application of current strategies and pattern matching algorithms to mammalian genomes will require the analysis of thousands to tens of thousands of individual clones for the generation of complete maps.

The present invention provides an alternative strategy for large-scale nucleic acid sequencing that does not require the generation of a sequence-ready map prior to sequencing. The invention combines and improves upon the whole genome shotgun (WGS) sequencing strategy and the clone-by-clone (CBC) sequencing strategy. In general, the invention provides a method for determining the sequence of a nucleic acid present in a clone by providing a plurality of clones in an array including predetermined axis, whereby the position of each clone in the array may be identified. Subsequently, multiple clones of a first axis are pooled and a first library is prepared from the pooled clones. Random reads are performed on the pooled clones thereby generating sequence coverage of the pooled clones. The method further entails pooling multiple clones of a second axis and preparing a second library from the pooled clones, wherein the second axis intersects the first axis at a nexus, and wherein the nexus includes at least one clone that is common to the first and second axis; performing random reads on the pooled clones of the second axis thereby generating sequence coverage of the pooled clones; cross-assembling the random reads of the first axis with the random reads of the second axis, thereby generating a sequence contig associated with the nucleic acid present in the nexus clone; and combining contigs and determining the sequence of the nucleic acid present in the clone.

Nucleic acid sequencing, as used herein, is the experimental process of determining the nucleotide sequence of a region of a nucleic acid such as DNA. As used herein, a "clone" is a vector comprising a nucleic acid sequence typically derived from the genetic complement of an organism. The vector can be chosen from any number of suitable vectors known to those skilled in the art of sequencing including cosmids, YACs (Yeast Artificial Chromosomes), megaYACS, BACs (Bacterial Artificial Chromosomes), PACs (P1 Artificial Chromosome), MACs (Mammalian Artificial Chromosomes), a whole chromosome, or a small whole genome. As used herein, a "Bacterial or Bacteriophage-Derived Artificial Chromosome" or "BBPAC" denotes a vector that is derived from a bacterium or bacteriophage such as a Bacterial Artificial Chromosome (BAC) which is an *E. coli* F element based cloning system, a P1-Derived Artificial Chromosome (PAC) or a bacteriophage-based gnomic vector. While not bound by the use of a particular vector, the invention envisions the use of BACs and PACs to construct large genomic DNA insert libraries (Mejia et al., Genome Res. 7:179, 1997; Shizuya et al., Proc. Natl. Acad. Sci. 89:8794, 1992) for inclusion in an array of the invention.

The nucleic acid sequence can be about 50 bp to about 5 Mbp in length. A "nucleic acid sequence" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogues thereof, such as phosphorothioates and thioesters, in either single stranded form, or a double-stranded helix. Double stranded DNA—DNA, DNA—RNA and RNA—RNA helices are possible. The term nucleic acid sequence, and in particular DNA or RNA sequences, refers only to the primary and secondary structure of a nucleic acid molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A "plurality of clones", as used herein, is a set of clones comprising nucleic acid targeted for sequencing by the method and system of the invention. A plurality of clones can, for example, constitute a genomic library. As used herein, the term "genomic library" refers to a mixture of clones constructed by inserting fragments of genomic nucleic acid into a suitable vector. The term "library" implies the existence of large numbers of different recombinants out of which only a few are of immediate interest to the investigator.

Genomic nucleic acid is typically DNA. Generally, genomic DNA can be the entire genome, a single chromosome, or a portion of a chromosome, such as the 300–400 kbp portions of chromosomal DNA typically contained within cosmids, BACs, YACs, megaYACs, PACs or MACs, of a given organism. A "genome", as used herein, is any portion of the inherited nucleic acid material, or its derivatives, of one or more individuals of any species. In particular, it comprises the DNA sequences that are to be determined or mapped. Furthermore, "genomics" is defined as the mapping, sequencing, and analysis of an organism's genome. As used herein, "functional genomics" is the development and application of experimental approaches to assess gene function by making use of the information and reagents provided by structural genomics.

For analysis, cosmids, BACs, YACs, megaYACs, PACs or MACs are distributed in an array. An "array", as used herein, is any matrix suitable for supporting and separating a plurality of clones. The array can be a grid pattern providing an x-axis and a y-axis. The size and density of the "grid" is determined by the size of the genome under analysis. For example, the individual clones of the plurality of clones are arranged on an array such that each clone is identifiable by unique coordinates within the array. Thus, if the plurality clones are arranged in a two-dimensional array, they are identified by unique x and y coordinates. The intersection of a given x-axis and y-axis is termed a "nexus". For example, cross-assembly of random reads between pairs of columns and rows (i.e., x and y axis of a two dimensional array) results in sequence contigs of 8–10 fold coverage that belong to specific clones at the points of the intersection of an x-axis and a y-axis (i.e., nexus). The pattern of the array can be based on the pattern and spacing of wells of a standard 96-well microtitre plate and the repetitive preparation of culture plates and may be carried out using equipment designed for working with this standard. However, it is understood that any matrix suitable for functioning as an array can be used with the present invention.

A similar strategy can be carried out using a three dimensional matrix rather than the two-dimensional matrix referred to above and illustrated in the examples. Thus, the array can be a "block" pattern providing an x-axis, a y-axis and a z-axis. The plurality of clones arranged in a three-dimensional array are identifiable by unique x, y and z coordinates. For example, if 1000 clones were arranged in a 10 times 10 times 10 matrix and random reads performed from groups of 10 clones pooled according to the planes of the matrix, the nexus would be the intersection of the matrix in x, y, and z dimensions. Thus, 1000 clones could potentially be cross-assembled in a three-dimensional matrix or array. This strategy may be also extended to matrices of greater dimensionality. As used herein, "assembly" or "cross-assembly" are terms of art that describe the process of placing fragments of DNA that have been sequenced into their correct position with regard to one another or within a chromosome.

The term "contig" is used in connection with DNA sequence analysis, and refers to reassembled contiguous stretches of DNA derived from two or more clones having contiguous nucleotide sequences. Thus, a contig is a set of overlapping clones that provides a partial contiguous sequence of a genome. A "scaffold" is defined as a series of contigs that are in the correct order, but are not connected in one continuous length. Contig maps represent the structure of contiguous regions of a genome by specifying overlap relationships among a set of clones. For example, the term "contigs" encompasses a series of cloning vectors which are ordered in such a way as to have each sequence overlap that of its neighbors. The linked clones identified by the method of the invention can then be grouped into contigs, either manually or, preferably, using appropriate computer programs. To confirm the correctness of the groupings, some of the contigs can be subjected to detailed restriction enzyme analysis, and the degree of physical overlap along with a physical map can be determined.

In general, the method of the invention organizes clones in an array such that DNA from each clone is pooled with clones in associated rows and columns and shotgun libraries are prepared from each pool. Sufficient random reads are collected from each library to generate 4–5 fold coverage of each clone in a row or column. Cross assembly of random reads between pairs of columns and rows results in sequence contigs of 8–10 fold coverage that belong to specific clones at the points of the intersection (i.e., nexus). Each assembled clone can then be finished using current methods for directed sequencing of individual subclones.

FIG. 1 depicts the general clone array pooled shotgun sequencing (CAPSS) strategy. A plurality of clones representing, for example, the genome of an organism, are organized in an array, and pools of DNA from each row and column are converted to a subclone library for sequencing. The sequence assembly of each clone is generated by cross-assembly of each row and column, shown as clone W in the schema. Clones A–F exemplify possible complications from other overlapping sequences in the array. Two DNA sequences are said to overlap when they share common subsequences, and this commonality is identifiable by techniques such as, for example, polymerase chain reaction (PCR) or DNA hybridization. The colors in clone A—F represent unique sequences. In this example, clone A and clone C share sequence, as do B and E. Cross assembly of R4+C5 will yield assembly from BAC A, and will include reads from the overlap in BAC C. Clones B and E will also generate contigs from both assemblies of R4+C5, and R8+C8. The generation of contigs at multiple locations in the grid distinguishes overlap that does not originate from the clone at the row/column intersection. Circles in A–F represent a perfect complete sequence contigs, with colors coding for different sequences. Note that shared sequence contig (in blue) between clone B and clone E will lead to assignment of the same contig to clone A and F, shown as an independent contig (in blue).

The scheme in FIG. 1 shows that CAPSS retains the advantages of both clone-by-clone (CBC) and whole genome shotgun (WGS) strategies, while overcoming their limitations. Pooling BACs dramatically reduces the effort for constructing and managing subclone libraries. To sequence the human genome using the CBC strategy, for example, at least 22,000 subclone libraries from individual BACs of 150 kb (assuming 10% overlaps) are required. However, if these BACs were organized and managed in a 148×148 two-dimensional format (FIG. 1) only 296 subclone libraries would be needed, considerably reducing the labor and management effort. The pooling procedure will not present any significant technical problems with clone normalization or representation.

Figure 2:
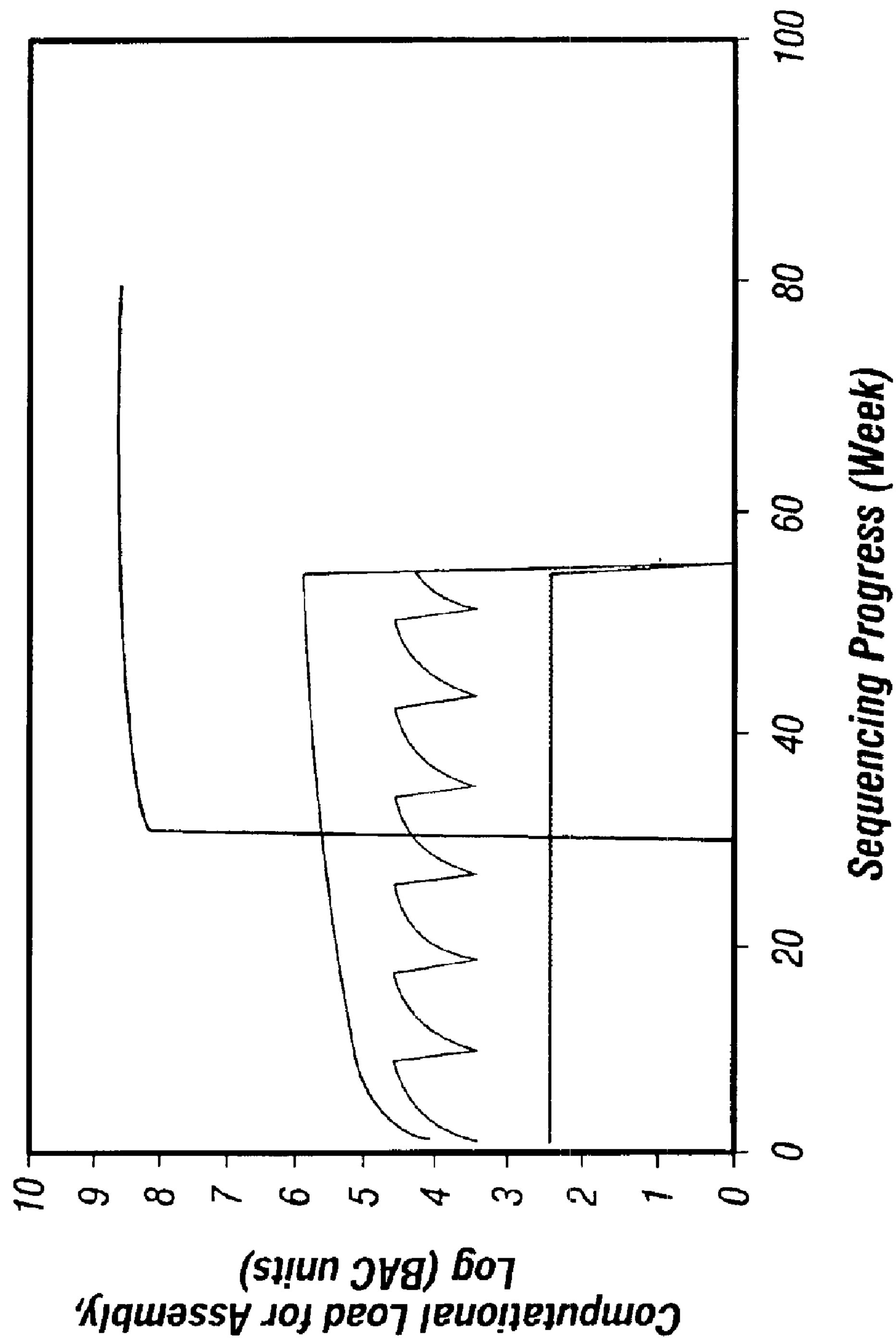
FIG. 2 is a line graph depicting the computational load for different sequencing strategies. Red, WGS; Green, CAPSS, 22,000 BACs in a single 148×148 array; Turquoise, 21,600 minimally overlapping BACs sequenced in 6 smaller 60×60 arrays; blue, CBC strategy for a total of 22,000 clones.

CAPSS provides the same average 8–10 fold DNA sequence coverage across the entire genome as CBC or WGS approaches (~$6.0\times10^7$ reads/3.0 Gb), however the reads can be assembled progressively with a modest amount of computational power. In the example of the 148×148 array for the human genome, approximately 203,000 reads are accumulated from each sub-library. Assembly of a pool of any row with any column (406,000 reads) requires about $1.8\times10^4$ fold more computation than assembly of a single 'typical' BAC, which is still a formidable task. Prior independent assembly of reads from each row and column in an array will however dramatically reduce peak computational requirements, as assembly of each intersecting BAC can be accomplished by comparison of these intermediate results, obviating the need to reiterate many computationally expensive pair-wise comparisons. A 203,000 read assembly represents about $4.5\times10^3$ times the load of a single BAC assembly and can be readily achieved in about 16 hours on a 800 MHz dual PIII processor-board with adequate RAM. A single such device costs less than $US20,000, and while less expensive machines can be applied with lower performance, slightly more costly computers can dramatically speed the result. This is one of the major advantages of CAPSS. The computational power needed to assemble each sub-library pair in pooled columns or rows is only about 1/90,000 of the power required for the WGS strategy assembly (see Table 1). When the time scale for the requirement of each of the assembly in a large genome project, distributed over one year, is considered, further economies of CAPSS relative to WGS are apparent (see FIG. 2).

TABLE 1

Computational Requirements for Assembly of 3 Gb Genome

| | CBC (22,000 BACs) | CAPSS (148 × 148 BACs) | CAPSS (60 × 60 BACs, 6 Arrays) | WGS (10 × Coverage) |
|---|---|---|---|---|
| Number of Reads/ Assembly | 3,000 | 203,000 | 83,300 | $6.0 \times 10^7$ |
| Computer Load Units/ Assembly | 1.0 | $4.5 \times 10^3$ | $7.6 \times 10^2$ | $4.0 \times 10^8$ |
| Total Number of Assemblies | $2.2 \times 10^4$ | 296 | 720 | 1.0 |
| Total Load/Genome | $2.2 \times 10^4$ | $1.3 \times 10^6$ | $5.5 \times 10^5$ | $4.0 \times 10^8$ |
| Approx Hardware Unit Cost (~$1,000's) | <20 | <20 | <20 | 80,000 |
| Estimated Total Hardware Cost ($1,000s) | 100 | 100 | 100 | 80,000 |

Simple DNA repeats will not confound CAPSS assemblies although long, low-frequency repeats can generate the same kind of ambiguities that are found in the CBC approach. The remedies for these complications are also the same as for CBC sequencing. The generation of double-ended sequences from subclones allows the formation of physical scaffolds along the length of each contig. This methodology was pioneered by the use of 'Sequence Mapped Gaps' (SMGs) in the first automated shotgun sequencing of a human cosmid and has since been addressed individually to resolve ambiguous assemblies. In extreme cases, single BACs in arrays can be addressed individually to resolve the ambiguous assemblies.

In another embodiment, the invention provides a method for mapping a genome. As used herein, "mapping" is defined as the process of determining the positions of genes and the distances between them on a chromosome. Mapping is accomplished by indentifying unique genome markers, such as expressed sequence tags (ESTs) or sequence tagged sites (STSs), and localizing these markers to specific locations on a chromosome. An "expressed sequence tag" (EST) is defined as a partial sequence of a cDNA clone that can be used to identify sites in a gene. A "sequence tagged site" (STS) is defined as a unique occurrence of a short, specific length of DNA within a genome whose location and sequence are known and that can be detected by PCR. An STS is used to orient and identify mapping data for the construction of physical genome maps.

The method of the invention envisions developing physical maps, genetic maps, and/or cytogenetic maps from the sequencing data generated by the method. The types of markers identified will differentiate the map produced. A "marker" is defined as a physical location on a chromosome that can be reliably monitored during replication and inheritance. For example, the process of genotyping utilizes markers to organize the genetic information found in individual DNA samples and to measure the variation between such samples. As used herein, a "physical map" identifies the physical locations (and order) on chromosomes of identifiable areas of DNA sequences such as restriction sites, genes, coding regions, etc. Physical maps are used when searching for disease genes by positional cloning strategies and for DNA sequencing. Clone-based physical maps have been extremely useful as the framework for many types of structural and biological studies and have been constructed for several model organisms including *E. coli, C. elegans, D. melanogaster* and *S. cerevesiae* (Kohara et al., *Cell,* 50:495, 1989; Oliver et al., *Nature,* 357:38, 1992; Sulston et al., *Nature,* 356:37, 1992; Merriam et al., *Science,* 254:221, 1991).

The invention also provides a mechanism for generating sequence information so that genotypic variations, including mutations and polymorphisms, can be identified. This information can be used to study genotype variations between affected and healthy individuals wherein specific regions of the genome that may be inherited with, or "linked" to, disease are determined. Thus, the invention facilitates the process of linkage analysis for the development of a "genetic map" or "linkage map" that provides the relative positions of genetic loci on a chromosome. A "loci", as used herein, is the location of a gene or other marker on the surface of a chromosome. A "genetic mutation" is defined as an inheritable alteration in DNA or RNA resulting in a change in the structure, sequence, or function of a gene. A "polymorphism" is defined as an individual difference in DNA. For example, a single nucleotide polymorphism (SNP) is a change in a single base pair at a particular position along the DNA strand. When an SNP occurs, the gene's function may change, as seen in the development of bacterial resistance to antibiotics or of cancer in humans. Thus, the method of the invention provides a mechanism for rapidly determining the genomic sequence of individuals and identifying genetic polymorphisms that indicate a predisposition to a particular disease. A "genetic polymorphism" can be defined as the occurrence of one or more different alleles at the same locus in a one percent or greater of a specific population. Alleles are different forms of a gene that occupy the same position on the chromosome. A "polymorphic marker" is defined as a length of DNA that displays population-based variability so that its inheritance can be followed.

The invention provides a method and system for the rapid and efficient sequencing of large nucleic acid sequences. Once obtained, a nucleic acid sequence can be used to identify regions of interest within the sequence. For example, the nucleic acid sequence may encode a polypeptide. The sequence information can be used to generate the amino acids sequence of the polypeptide in silico. The amino acid sequence can be annotated to gather additional information about the encoded polypeptide. As used herein, "annotation" of a sequence is defined as the elucidation and description of biologically relevant features of a polypeptide encoded by a particular nucleic acid sequence. This information can be added to a sequence database and generally provides the following items: a) function(s) of the polypeptide; b) post-translational modification(s) (i.e., carbohydrates, phosphorylation, acetylation, GPI-anchor); c) domains and sites (i.e., calcium binding regions, ATP-binding sites, zinc fingers, homeobox, kringle); d) secondary structure; e) quaternary structure (i.e., homodimer, heterotrimer); f) similarities to other polypeptides; g) disease(s) associated with deficiencie(s) in the polypeptide; h) sequence conflicts or variants.

Thus, in order to facilitate the discovery and characterization of genes and other important biological information within a nucleic acid sequence derived from a genome, a variety of DNA analysis programs can be integrated with the present invention. Analysis of genomic sequences by these programs can be completely automated. Such analysis programs can include gene prediction programs, protein and DNA homology searches, and programs to identify repeats, polyA sites, CpG islands, promoters, start/stop codons, and open reading frames. Data from each program can be stored and accessed by those users participating in the sequencing effort. Alternatively, subscribers can be granted limited access to the database of information generated by the analysis programs.

As previously noted, sequence (nucleic acid sequence and/or amino acid sequence) analysis programs can be integrated with the present invention. Examples of programs that can be used in conjunction with the present invention include programs such as BLAST (Basic Local Alignment Search Tool) which is a program for searching biosequence databases and was developed and is maintained by the National Center for Biotechnology Information (NCBI). BLAST locates patches of regional similarity instead of calculating the best overall alignment using gaps. The program then uses a scoring matrix to rank these matches as positive, negative or zero. If the initial match is scored highly, the search is expanded in both directions until the ranking score falls off. There are several versions of BLAST: BLASTP which searches a protein database, BLASTN to search a nucleotide database, TBLASTN which searches for a protein sequence in a nucleotide database by translating nucleotide sequences in all six reading frames, BLASTX which can search for a nucleotide sequence against a protein database by translating the query via all six reading frames, gapped-BLAST, and psi-BLAST. BEAUTY (BLAST Enhanced Alignment Utility) is a tool developed at Baylor College of Medicine which uses BLAST to search several custom databases and incorporates sequence family information, location of conserved domains, and information about any annotated sites or domains directly into the BLAST query results.

Additional sequence analysis programs include: 1) BLITZ which is an ultra-fast protein database search utilizing the MPsearch algorithm; 2) BLOCKS which is a database of ungapped multiple alignments for protein/peptide families in PROSITE; and 3) CLUSTAL W which is a general purpose program for multiple alignments of DNA and protein sequences.

The aforementioned sequence analysis programs can be used in conjunction with the invention to identify sequence or structural similarities between sequences. The sequences generated by the invention (nucleic acid and/or amino acid) can be compared to those sequences already available in databases known to those of skill in the art. For example, GenBank is the NIH genetic sequence database. It provides an annotated collection of publicly available DNA sequences (http://www.ncbi.nlm.nih.gov). There are approximately 2,162,000,000 bases in 3,044,000 sequence records as of December 1998. GenBank is part of the International Nucleotide Sequence Database Collaboration, which is comprised of the DNA DataBank of Japan (DDBJ), the European Molecular Biology Laboratory (EMBL), and GenBank at NCBI. These three organizations exchange data on a daily basis. EMBL is Europe's primary nucleotide sequence resource. The main sources for DNA and RNA sequences are direct submissions from individual researchers, genome sequencing projects and patent applications. Thus, the sequences identified by the invention can be compared to sequences in the aforementioned databases and used to, for example, identify consensus sequences, i.e., commonly occurring amino acid or nucleotide at each position of an aligned series of proteins or polynucleotides. The consensus sequence information can be used to generate a consensus map which provides the location of all consensus sequences in a series of multiply aligned proteins or polynucleotides. Consensus sequence information is also useful for identifying a conserved sequence, i.e., a sequence within DNA or protein that is consistent across species or has remained unchanged within the species over its evolutionary period.

Sequence information generated by the invention can also be used to identify motifs. As used herein, a "motif" provides a pattern of DNA sequence that is similar for genes of similar function. Also a pattern for protein primary structure (sequence motifs) and tertiary structure that is the same across proteins of similar families. Such motifs can be identified by aligning a sequence generated by the invention with a sequence or sequences already available in a database. For example, in pairwise alignment two sequences are padded by gaps so that they are the same length and so that they display the maximum similarity on a residue to residue basis. An optimal pairwise alignment is an alignment which has the maximum amount of similarity with the minimum number of residue 'substitutions'. In a multiple alignment, a set of sequences can be arranged in a table such that each row of the table consists of one sequence padded by gaps. The columns of the table highlight similarity (or residue conservation) between positions of each sequence.

In another embodiment, the invention provides a system for sequencing a genome including a means or mechanism for arranging the plurality of clones in a array, wherein the array includes predetermined axis and wherein each clone is identifiable in the array; a means or mechanism for pooling clones of a first axis and preparing a first library from the pooled clones; a means or mechanism for performing random reads on the pooled clones of the first axis, thereby generating sequence coverage of the pooled clones; a means or mechanism for pooling the clones of a second axis and preparing a second library from the pooled clones, wherein the second axis intersects the first axis at a nexus, and wherein the nexus includes at least one clone that is common to the first and second axis; a means of mechanism for performing random reads on the pooled clones of the second axis, thereby generating sequence coverage of the pooled clones; a means or mechanism for cross-assembling the random reads of the first axis with the random reads of the second axis, thereby generating a sequence contig; a means or mechanism for combining multiple sequence contigs derived from a plurality of nexuses to construct a map of the clones relative to the genome; and a means or mechanism for determining the sequence of the genome by means of the map.

It may be appreciated that the method described herein may be used in conjunction with manual, semi-automated or fully automated sequencing apparatus known in the art. In manual sequencing the scientist typically reads the sequence off an autoradiograph taken from a gel, on which radioactive or chemiluminescent DNA fragments have been separated according to size by electrophoresis. Such techniques are well known in the art and are described for example in Sambrook, J et al (1989) Molecular Cloning: a laboratory manual, Cold Spring Harbor Laboratory, Cold Spring Harbor, N.Y. The sequence is then conveniently entered into a computer to facilitate observation and/or manipulation of the sequence using appropriate computer software. However, manual sequencing is being circumvented by semi-automated or fully automated sequencing apparatus which can not only determine the sequence of a particular polynucleotide, but can input this information directly into a computer comprising appropriate sequence handling computer software.

It is understood that any apparatus suitable for polynucleotide sequencing can be used in the present invention, including robotic devices. Such devices provide mechanisms whereby random reads are performed automatically on pooled clones. Various non-limiting examples of apparatus, components, assemblies and methods known to those of skill in the art of automated sequencing and robotics are encompassed by the invention. For example, it is contemplated that a means for arranging clones in an array can be accomplished by an automated nanodispensing. An example would be an ink-jet dispensing system. Because of the speed and capability of the ink-jet dispensing system, sequencing can be made very small and very rapid. For example, the array can be functionally linked to microchannels that will move fluids by microfluidics. Thus, microfluidics can be used to pool clones in an x-axis and y-axis to facilitate the sequencing of the clones.

Multiwell arrays are well known in the art and are exemplified, for example, by those described in U.S. Pat. Nos. 3,111,489, 3,540,856, 3,540,857, 3,540,858, 4,304, 865, in U.K. Patent 2,000,694 and in European Patent Application 0,098,534. Typically, such arrays are provided as so-called microtiter plates and are used for examination of the physical, chemical or biological characteristics of a quantity of samples in parallel. The samples to be examined are arranged in array form in small cavities or wells that provide ninety-six depressions or cylindrical wells of about 0.66 cm in diameter and 1.3 cm deep, arranged in a 12×8 regular rectangular array, spaced about 0.9 cm. center to center. A recent form of another multiwell test plate employs the same footprint as the ninety-six well plate but provides 384 wells arranged as four blocks of ninety-six wells each, the wells, of course, being much lesser in diameter than those of the ninety-six well plate.

In yet another embodiment, the invention provides a computer-assisted method for determining the sequence of a genome using a programmed computer including a processor, an input device, and an output device, the method including inputting into the programmed computer, through the input device, data including the location of each clone of a plurality of clones in an array comprising predetermined axis, wherein the location of each clone is identified by unique coordinates that describe the position of each clone in the array Thus, the invention further provides a computer-assisted method for sequencing a target nucleic acid using a programmed computer including a processor, an input device, and an output device, by inputting into the programmed computer, through the input device, data including the positions of clones in an array, the pooling scheme of the various axis, and sequence information generated by random reads of the pooled clones of the axis. A processor is then used to cross-assemble the random reads and generate a sequence contig. The processor is further utilized to combine multiple sequence contigs derived from a plurality of clones to construct a map of the clones relative to the genome. The sequence is determined by the processor and the information outputted to the output device.

Aspects of the invention may be implemented in hardware or software, or a combination of both. However, preferably, the algorithms and processes of the invention are implemented in one or more computer programs executing on programmable computers each comprising at least one processor, at least one data storage system (including volatile and non-volatile memory and/or storage elements), at least one input device, and at least one output device. Program code is applied to input data to perform the functions described herein and generate output information. The output information is applied to one or more output devices, in known fashion.

For example, in the present invention, the sequences of the clones are assembled into the complete sequence of the subclone by matching overlaps. The subclone sequences are then assembled into the sequence of the mapped clone. The sequences of the mapped clones are assembled into the complete sequence of the genome by matching overlaps. Computer programs are available for these tasks (Rodger Staden programs, Cambridge, UK; DNAStar, Madison, Wis.). Following sequence assembly, current analysis practice includes similarity and homology searches relative to sequence databases (Genbank, Bethesda, Md.; EMBL, Cambridge, UK; Phil Green's GENEFINDER, Seattle, Wash.) to identify genes and repetitive elements, infer function, and determine the sequence's relation to other parts of the genome and cell. Each program may be implemented in any desired computer language (including machine, assembly, high level procedural, or object oriented programming languages) to communicate with a computer system. In any case, the language may be a compiled or interpreted language.

Each such computer program is preferably stored on a storage medium or device (e.g., ROM, CD-ROM, tape, or magnetic diskette) readable by a general or special purpose programmable computer, for configuring and operating the computer when the storage media or device is read by the computer to perform the procedures described herein. The inventive system may also be considered to be implemented as a computer-readable storage medium, configured with a computer program, where the storage medium so configured causes a computer to operate in a specific and predefined manner to perform the functions described herein.

Thus, in another embodiment, the invention provides a computer program, stored on a computer-readable medium, for sequencing a target polynucleotide. The computer program includes instructions for causing a computer system to: 1) distribute a clone in a two-dimensional grid; 2) pool clones in an axis; and 3) control sequencing of the pooled clones.

In another embodiment, the invention provides a multi-user method for sequencing a genome. Once an array has been established and the positions of particular clones in the array are recorded, the clones can be sequenced at remote locations. The sequence information generated at various locations can be communicated to a central location, such as a server, and compiled. The compilation of sequence information can entail the construction of maps. Thus, the invention further provides a computer system including a database incorporating records of the location of each clone of a plurality of clones in an array having predetermined axis; a database including random reads of the clones inputted by one or more users of the database; a processor for cross-assembling the random reads of the clones; a processor for determining contiguous regions among the cross-assembled random reads and for generating a contig map based upon the identified contiguous regions; and a means for outputting to an output device the results of the contig map.

It is therefore immediately evident that a computer program designed for ordering of the fragments into a contiguous over-lapping arrangement may be provided which is suitable for use with the method of the present invention when using manual, semi-automated, and/or fully automated sequencing apparatus. For example it may be possible to provide suitable software for use in conjunction with a semi-automated or fully automated sequencing apparatus such that the fragments generated using the method of the present invention may be sequenced using a single apparatus linked to a computer comprising the computer software. The sequences of the various fragments are determined using the sequencing apparatus, and the software is able order the fragments into a contiguous over-lapping arrangement. Thereafter the software is able to determine the sequence of said nucleotide from said contiguous arrangement and provided the user with a single nucleotide sequence corresponding to the original nucleic acid sequence. A semi-automated or fully automated sequence apparatus with a dedicated computer may be provided with the computer program preloaded into the computer's memory.

In yet another embodiment, the invention provides a method for indexing a nucleic acid sequence of an organism including providing a first sequence from a first organism according to the a method of the invention; indexing the sequence of the first organism; comparing the indexed sequence of the first organism with a non-indexed sequence obtained from a second organism; and identifying a sequence in the non-indexed sequence which is common to the indexed sequence, thereby indexing the non-indexed sequence of the second organism.

It is further envisioned that the method and systems of the present invention can be integrated with other methods of sequence analysis. A wide variety of cytogenetic, genetic, and physical mapping data is available on a genomic, chromosomal, or local scale. Methods and resources used to build these maps vary significantly in their basic principles and resolution power, assessment of position for a given marker often poses both fundamental and practical problems and difficulties. The present invention further provides for the integration of sequencing and mapping information by cross-indexing the genomic sequences generated by the present invention with information already available for other genomes. For example, cross-species relationships are often critical components for identifying functional genes that are evolutionarily conserved. The sequence information generated by the invention can be compared to gene indices of other species in order to facilitate the identification of common genomic structures, transcript clusters, or predicted exons.

Thus, the information generated by the invention can be indexed and compared with the information available from other similarly indexed or non-indexed databases. Comparative sequence analysis is a powerful and increasingly important method for genome analysis and annotation. Since functional regions tend to be more highly conserved than non-functional DNA, local sequence similarity usually indicates functionality. This fact can be used to detect functional sites such as protein-coding regions or regulatory elements in large genomic DNA sequences. As part of this effort, an indexed genome can be used to increase the effectiveness of algorithms used for genome alignment over large data sets. Indexing allows matches to be found in a large data set without exhaustively scanning the data. Thus, indexing can be used to find a set of possible positions of alignment without scanning through all the stored sequences in their entirety. For example, gene indexing can facilitate gene discovery through partitioning and assembling EST databases into a non-redundant set of gene-oriented clusters.

Furthermore, significant data sets (microarray results, gene maps, large parts of NCBI databases, excluding the sequence) benefit from indexing and can therefore be retrieved interactively and compared with the sequence information generated by the invention. Sequence indexes can be used in comparative genomics thus allowing for the transfer of information between, for example, human, rat and mouse genomes. Alternatively, indexing can be used in data mining of sequences. The sequence information generated by the invention can be compared with several genomes and motifs common to all examined genomes can be identified.

EXAMPLES

Computer Simulation of CAPSS

The feasibility of the CAPS S strategy was demonstrated using a computer simulation of fully sequenced human BAC clones. Randomly selected BAC clones were organized into a 5×5 and a 10×10 clone array. Three-fold sequence coverage of random pair-end reads, each 400 base pair in length and 10 kb apart, were generated for each BAC clone in the array. Random reads generated from clones in the same row or column were pooled. In order to identify reads from an individual clone from within the pool, two cycles of comparison were performed. In the first round, pooled reads from a row and a column were assembled into separate groups of contigs using the PHRAP program (Bonfield et al., *Nucleic Acids Res.* 24:4992, 1995). Reads from the column were then compared against the contigs assembled from the row and vice versa using the BLASTN program (Altschul et al., *Nucleic Acids Res.* 25:3389, 1997). The BLASTN comparison results were analyzed based on the E value and significance score. Reads that had a score greater than 80 and E value lower than 0.001 were considered true match and therefore assigned to the BAC clone locates at the intersection of the column and the row. In the second round, assembly was performed on each BAC using matched reads identified in round one, and the resulting contigs were searched against reads from the column and the row. Based on the same criteria as the first round, reads having true matches were assigned to individual BAC clones.

To test the efficiency of assigning reads back to individual BAC clones (i.e., homing efficiency), five randomly selected BAC clones were examined in both 5×5 array and 10×10 arrays. In the first round for the 5×5 array, 11,508 out of a possible 12,472 reads were assigned back to the BAC clone correctly and the homing efficiency was 92.27%. Only 4 reads were mis-assigned, providing an error rate of about 0.02% (see Table 2). Similarly, in the 10×10 array, 11,654 out of 12,742 reads were correctly assigned with a 93.4% homing efficiency and a 0.04% error rate (see Table 2). Interestingly, among these five BAC clones, the homing efficiency was quite different, ranging from 85% to 99%. It appears that the homing efficiency does not change with the size of the clone array but is closely related to the content of repetitive sequences in the BAC clone (see Table 2). However, even for the clone containing a very high percentage of repetitive sequences, a relatively high homing efficiency is achieved, indicating that CAPSS is a very robust method.

TABLE 2

Homing efficiencies of BAC clones with different repetitive sequence contents.

| BAC | hmkq | hmyd | haof | hmyt | hmgr | Average |
|---|---|---|---|---|---|---|
| Length (bp) | 166257 | 145820 | 184834 | 177317 | 157872 | |
| #of repetitive bases | 64406 | 70021 | 78830 | 89619 | 100125 | |
| Percentage of repeats | 38.7 | 48.0 | 42.6 | 50.0 | 63.4 | |
| Total # of reads | 2492 | 2184 | 2772 | 2656 | 2368 | 12472 |
| clone array | 5 × 5 clone array | | | | | |
| Assembled reads in first round | 2464 | 1956 | 2712 | 2364 | 2012 | 11508 |
| Homing efficiency % | 98.9 | 89.56 | 97.8 | 89.0 | 84.9 | 92.2 |
| Errors | 0 | 0 | 0 | 0 | 2 | 0.02% |
| Assembled reads in second round | 2474 | 2030 | 2738 | 2444 | 2074 | 11760 |
| Homing efficiency % | 99.3 | 92.9 | 98.8 | 92.0 | 87.6 | 94.2 |
| Errors | 0 | 0 | 0 | 0 | 16 | 0.1% |
| clone array | 10 × 10 clone array | | | | | |
| Assembled reads in first round | 2460 | 2020 | 2722 | 2426 | 2026 | 11654 |
| Homing efficiency % | 98.9 | 94.0 | 98.2 | 91.3 | 85.6 | 93.4 |
| Errors | 0 | 0 | 0 | 0 | 4 | 0.04% |
| Assembled reads in second round | 2470 | 2038 | 2740 | 2468 | 2078 | 11749 |
| Homing efficiency % | 99.1 | 93.3 | 98.8 | 92.9 | 87.8 | 94.5 |
| Errors | 0 | 0 | 0 | 0 | 20 | 0.2% |

The simulation data clearly indicate the feasibility of the CAPSS strategy the sequence read assignment strategy of the invention can be used in conjunction with other sequencing methods. For example, paired-end sequencing can be used in conjunction with CAPSS. In the paired-end scheme, a clone is considered to match whenever at least one of its end reads has significant match. Since the chance of both ends of a clone being in a repetitive region is relatively small, the homing efficiency can be increased when sequences from both ends of a clone are used for comparison. For example, in the hmkq clone, only 84% of reads have matches with an E value less than 0.001. Using the pair-end sequencing approach, the homing efficiency is increased to 99.3%. Such improvement is even more striking in the clone with high content of repetitive sequences. For example, the hmyd clone contains 48% sequences and only 74% of the reads have matches. Using the pair-end method, the final homing efficiency is 92.9%.

In addition, the invention can be used in conjunction with a program that eliminates repetitive sequences from reads. Such "masking" programs include RepeatMask (Smith & Green)) which can be used to search against unmasked contigs. However, since repeat-masking imposes an additional computational load, there is a pay-off between computing time and homing efficiency. To maximize homing efficiency and minimize computation time, a two-step protocol can be used where, following comparison between unmasked reads and repeat-masked contigs, remaining reads are repeat-masked and compared with the unmasked contigs.

Finally, incorrect assignment of reads often results from matching between a short stretch of sequence and a contig. Usually such match has relatively low score and tends to be assigned to clones containing high amount of repetitive sequences (Table 2). These errors can be reduced dynamically by adjusting the score used to filter the match results, and developing procedures for manual examination of matches that generate ambiguous matches that produce conflicting assemblies.

Application of CAPSS to large genomes for which no complete sequence-ready map exists further illustrates the power of the method. For example, a 140×140 array would be suitable for sequencing the mouse genome, where accumulated efforts over the past decade have resulted in a high-resolution genetic map and an STS based physical map with around 12,000 markers. About 2,800 of these markers have been used to identify corresponding BAC clusters across the genome. In addition, BAC-end sequencing representing 10-fold clone coverage is underway.

Each of currently available murine BACs is of average size 200 kbp, and an array containing approximately 20,000 clones represents about 4.0 Gb, or 1.3 fold of genomic coverage. Accumulation of $6.0\times10^7$ sequence reads for the entire collection yields approximately 215,000 reads per row or column, and provides an average total of 3,000 reads that originate from each BAC at the points of intersection, or about 7.5-fold coverage per BAC. This is sufficient to enable assembly of large contigs from each clone at points of intersection, but represents less coverage than the 8–10 fold that would be ideally achieved in an array formed by only minimally overlapping BACs.

Further coverage of each BAC will be automatically generated within the matrix of the assemblies that are completed for the entire array. FIG. 1 shows that fortuitous overlap with other clones in the same row or column, directly increases the depth of sequence coverage in the assembly of the clone at the point of intersection. These overlapping fragments can be distinguished from a second class of contigs within each assembly that contain reads from both rows and columns but are derived from pairs of overlapping clones where neither are at the row/column intersection. The reads in these 'unrelated overlaps' are also found in contigs from the cross assemblies for which each unrelated BAC is the primary assembly target. A computer routine is sufficient to correlate these events and ultimately assign each initial contig to its correct final assembly based upon the contig positions in the different row vs. column assemblies.

Reduced array structures can also be applied to further simplify the analysis of the mouse genome example. For example, the 2,809 BACs from the currently available BAC framework map can first be sequenced in a 53×53 format. Since these BACs do not overlap with one another, sequence contig assignment will be unambiguous. When each BAC in this array is assembled a second set can be identified by physical mapping or BAC end sequence assignment. After 6 iterations of this process, the total sequences would provide 1.2 fold coverage of the genome. Alternatively, mapped BACs can be combined with a selection of random BACs to form a slightly larger array. After these BACs are sequenced, further selection and sequencing of minimally overlapping BACs will complete the whole genome. As a general strategy, the use of these sub-arrays provides the advantages of CAPSS while obviating any possible operational problems due to unexpected clone overlap in poorly mapped genomes. The smaller arrays also present a more manageable logistics problem for existing sequencing centers.

The invention can be also used in combination with whole-genome shotgun sequencing to enable a complete genome assembly. CAPSS data can provide an initial assembly of each clone, and these contigs could be used to select sequence reads from a pool of WGS data for subsequent cycles of clone-linked assemblies. This is a particularly attractive strategy as it maximizes the diversity of sequence data that can be combined to produce a final genome assembly.

The combination of CAPSS and WGS data may be the best solution for analyzing large genomes that have minimal mapping data available. This strategy would utilize arrays that contain sufficient clones to ensure complete genomic coverage, and the DNA sequencing effort would be divided between the CAPSS and WGS components. For example, a 3 Gb genome for which an average two-fold BAC clone coverage array of 200×200 clones is constructed could have 40 million reads produced for the entire array. CAPSS assemblies in this case would have approximately 6–7.0 fold coverage at the points of intersection of rows and columns, which would be predicted to generate contigs of sufficient length to localize the information from a further $2.0\times10^7$ WGS reads.

Current approaches to whole genome sequencing utilize $6\times10^7$ reads of average length of 500 bases to generate 10× coverage of a 3.0 Gb genome. If N random reads provide 10× coverage of a genome the number of first pass searches needed to sort the random reads into individual overlapping contigs is estimated by:

$$\sum_{i=1}^{N/10}(N-10i)$$

which is approximated by $\sim N^2/20$. Thus the computation time for assembling random shotgun reads without any pre-sorted keys such as sequence contigs from individual BACs roughly scales with the square of the size of the genome. For example, Table 1 shows the results generated by the invention when $6.0\times10^7$ total random reads are collected. In the example clones are distributed in a 148×148 array necessitating that about 203,000 reads be collected from each subclone library. The relative computational load units required were calculated for each scenario, assuming the load to assemble 3,000 reads for each BAC equals to one. This can readily be achieved in less than 15 minutes using a Pentium computer costing less than $20,000. To estimate the computational load, the method of the invention calculates the search equivalent (in BAC units) for the first pass of assembling random reads into contigs of multiple fold coverage. If the unique sequence at both ends of a contig are determined to find their matches in other contigs the number of searches will be much smaller compared to the first pass search for clustering random reads. Thus, the computational load for cross assembly of pre-assembled rows and columns is not taken into account in the estimation of total load. To compare the computational requirement for different sequencing strategies (see FIG. 2), it can be assumed that the sequencing capacity allows random read collection of 10× coverage of a 3 Gb genome in 52 weeks and the sequencing load is spread out uniformly over the same period. In WGS, the assembly will not be productive until half of the sequence reads have been collected and will continue after the sequencing phase is finished.

Additional advantages of using the method and system of the invention to sequence complex genomes include: 1) Unlike WGS sequencing, each project will progressively yield regions with full sequence coverage. As each new row or column is completed, all intersecting BACs are fully covered, and consequently clones of high biological interest can be prioritized for early finishing. In addition, gap closing can proceed in parallel with sequencing. This is an important advantage as subclone archives need not represent the whole genome, as they do in the WGS method; 2) Larger numbers of BACs with relatively small insert sizes (~100 kb) can be used with the invention since the number of subclone libraries from pooled BACs increases only with the square root of the number of clones in the BAC array. This is an extremely useful technical advantage as library construction and growth of these smaller clones is considerably easier than for larger inserts. Recent development of an inducible multi-copy BAC cloning vector raises the possibility of pooling clones before growth, which would even further simplify CAPSS; and 3) Many sequencing centers can participate in different phases of a CAPSS project independently. Large centers can focus on, for example, sequencing multiple rows or columns of BACs to completion and assemble the sequence contigs assigned to individual BACs progressively, and smaller groups can close gaps in those BACs of their scientific interest. This is an important advantage as it follows the current international trend of allowing the cultivation of both small and large sequencing centers.

A number of embodiments of the invention have been described. Nevertheless, it will be understood that various modifications may be made without departing from the spirit and scope of the invention. Accordingly, other embodiments are within the scope of the following claims.

What is claimed is:

1. A method for determining a sequence of a target nucleic acid, comprising:

a) providing a plurality of clones containing fragments of the target nucleic acid in an array comprising predetermined axes, whereby the position of each clone in the array may be identified;

b) pooling multiple clones of a first axis and preparing a first library from the pooled clones;

c) performing random sequencing reads on the pooled clones of b), thereby generating sequence coverage of the pooled clones;

d) pooling multiple clones of a second axis and preparing a second library from the pooled clones, wherein the second axis intersects the first axis at a nexus, and wherein the nexus comprises at least one clone that is common to the first and second axis;

e) performing random sequence reads on the pooled clones of d) thereby generating sequence coverage of the pooled clones;

f) cross-assembling the random sequence reads of c) with the random sequence reads of e), thereby generating a sequence contig associated with the nucleic acid present in the nexus clone;

g) repeating steps a) through f) to generate multiple contigs; and h) combining contigs of step g) and determining the sequence of the nucleic acid present in the pooled clones.

2. The method of claim 1, wherein the array is a two-dimensional array.

3. The method of claim 2, wherein the two-dimensional array comprises an x and y axis.

4. The method of claim 1, wherein each clone is compartmentalized.

5. The method of claim 2 or 4, wherein the location of each clone in the array is identified by unique coordinates that describe the location of the clone in the array.

6. The method of claim 1, wherein each random sequence read generates about 3 to 6 fold coverage of each clone.

7. The method of claim 1, wherein each random sequence read generates about 6 to 12 fold coverage of the nexus clone.

8. The method of claim 1, wherein the target nucleic acid comprises an organism genome.

9. The method of claim 1, wherein the array is a three-dimensional array.

10. The method of claim 9, wherein the three-dimensional array comprises an x, y and z axis, and wherein the clones are pooled according to intersecting planes of the x, y and z axis of the three-dimensional array.

11. The method of claim 1, wherein the library is a shotgun library.

12. The method of claim 1, wherein the target nucleic acid is derived from a genome.

13. The method of claim 1, wherein the clone library has average DNA insert size of about 500 kb.

14. The method of claim 1, wherein the clone library has average DNA insert size of about 250 kb.

15. The method of claim 1, wherein the clone library has average DNA insert size of about 125 kb.

16. The method of claim 1, wherein the clone library comprises a cloning vector selected from the group consisting of bacterial, yeast and phage cloning vectors.

17. The method of claim 16, wherein the vector is selected from the group consisting of cosmid, BAC, YAC, megaYAC, MAC or PAC.

18. The method of claim 1, wherein the clone library has at least two-fold coverage of the genome.

19. The method of claim 1, wherein the genome includes a mammalian genome.

20. The method of claim 19, wherein the mammalian genome is a mouse genome.

21. The method of claim 1, wherein each clone is contained in a cell.

22. The method of claim 21, wherein the cell is a bacterial cell.

23. The method of claim 21, wherein the cell is a yeast cell.

24. The method of claim 21, wherein the cell is a mammalian cell.

25. A method for preparing a contig map comprising:

a) preparing a genomic library comprising a plurality of clones by inserting DNA fragments from a genome into vectors;

b) arranging the clones in an array in predetermined axes, whereby the position of each clone in the array may be identified;

c) pooling the clones of a first axis and preparing a first library from the pooled clones;

d) performing random sequence reads on the pooled clones of c), thereby generating sequence information from the pooled clones;

e) pooling the clones of a second axis and preparing a second library from the pooled clones, wherein the second axis intersects the first axis at a nexus, and wherein the nexus comprises at least one clone that is common to the first and second axis;

f) performing random sequence reads on the pooled clones of e), thereby generating sequence coverage of the pooled clones;

g) cross-assembling the random sequence reads of d) with the random sequence reads of f); and h) identifying contiguous regions among the cross-assembled random sequence reads of g), thereby generating a contig map.

26. The method of claim 25, wherein the array is a two-dimensional array.

27. The method of claim 26, wherein the two-dimensional array comprises an x and y axis.

28. The method of claim 25, wherein each clone is compartmentalized.

29. The method of claim 25, wherein each random sequence read generates about 3 to 6 fold coverage of each clone.

30. The method of claim 25, wherein each random sequence read generates about 6 to 12 fold coverage of the nexus clone.

31. The method of claim 25, wherein the array is a three-dimensional array.

32. The method of claim 31, wherein the three-dimensional array comprises an x, y and z axis, and wherein the clones are pooled according to intersecting planes of the x, y and z axis of the three-dimensional array.

33. The method of claim 26 or 32, wherein the location of each clone in the array is identified by unique coordinates that describe the location of the clone in the array.

34. The method of claim 25, wherein the library is a shotgun library.

35. The method of claim 25, wherein the clone library has average DNA insert size of about 500 kb.

36. The method of claim 25, wherein the clone library has average DNA insert size of about 250 kb.

37. The method of claim 25, wherein the clone library has average DNA insert size of about 125 kb.

38. The method of claim 25, wherein the clone library comprises a cloning vector selected from the group consisting of bacterial, yeast, and phage cloning vectors bacterial, yeast or phage cloning vectors.

39. The method of claim 38, wherein the vector is selected from the group consisting of cosmid, BAC, YAC, megaYAC, MAC or PAC.

40. The method of claim 25, wherein the clone library has at least two-fold coverage of the genome.

41. The method of claim 25, wherein the genome is a mammalian genome.

42. The method of claim 41, wherein the mammalian genome is a mouse genome.

43. A system comprising a processor for sequencing a genome comprising:

a) means for arranging a plurality of clones in a array, wherein the array comprises predetermined axes and wherein each clone is identifiable in the array;

b) means for pooling clones of a first axis and preparing a first library from the pooled clones;

c) means for performing random sequence reads on the pooled clones of c), thereby generating sequence coverage of the pooled clones;

d) means for pooling the clones of a second axis and preparing a second library from the pooled clones, wherein the second axis intersects the first axis at a nexus, and wherein the nexus comprises at least one clone that is common to the first and second axis;

e) means for performing random sequence reads on the pooled clones of e), thereby generating sequence coverage of the pooled clones;

f) means for cross-assembling the random sequence reeds of d) with the random sequence reads of f), thereby generating a sequence contig associated with the nucleic acid present in the nexus clone;

g) means for combining multiple sequence contigs derived from a plurality of nexuses to construct a map of the clones relative to the genome; and h) means for determining the sequence of the genome by means of the map.

44. The system of claim 43, wherein the array is a two-dimensional array comprising a predetermined x and y axis.

45. The system of claim 43, wherein the clones are pooled according to the x and y axis of the two-dimensional array.

46. The system of claim 43, wherein the nucleic acid present in the plurality of clones collectively comprise the genomic DNA of an organism.

47. The system of claim 43, wherein the array is a three-dimensional array comprising an x, y and z axis.

48. The system of claim 43, wherein the clones are pooled according to intersecting planes of the x, y and z axis of the three-dimensional array.

49. The system of claim 45 or 48, wherein the location of each clone in the array is identified by unique coordinates that describe the location of the clone in the array.

50. The system of claim 43, wherein the library is a shotgun library.

51. The system of claim 43, wherein the nucleic acid is derived from a genome.

52. The system of claim 43, wherein the clone library has average DNA insert size of about 500 kb.

53. The system of claim 43, wherein the clone library has average DNA insert size of about 250 kb.

54. The system of claim 43, wherein the clone library has average DNA insert size of about 125 kb.

55. The system of claim 43, wherein the clone library comprises a cloning vector selected from the group consisting of bacterial, yeast, and phage cloning vectors bacterial, yeast or phage cloning vectors.

56. The system of claim 55, wherein the vector is selected from the group consisting of cosmid, BAC, YAC, megaYAC, MAC or PAC.

57. The system of claim 43, wherein the clone library has at least two-fold coverage of the genome.

58. The system of claim 43, wherein the genome includes a mammalian genome.

* * * * *